United States Patent [19]
Ryan et al.

[11] Patent Number: 5,929,055
[45] Date of Patent: Jul. 27, 1999

[54] THERAPEUTIC METHOD FOR MANAGEMENT OF DIABETES MELLITUS

[75] Inventors: Maria Emanuel Ryan, Huntington; Lorne M. Golub; Nungavaram S. Ramamurthy, both of Smithtown; Thomas F. McNamara, Port Jefferson, all of N.Y.

[73] Assignee: The Research Foundation of State University of New York, Albany, N.Y.

[21] Appl. No.: 08/880,945

[22] Filed: Jun. 23, 1997

[51] Int. Cl.$^6$ .......................... A61K 31/65; A61K 38/28; A61K 31/155

[52] U.S. Cl. .............................. 514/152; 514/3; 514/634; 514/866

[58] Field of Search ................................ 514/3, 152, 634, 514/866

[56] References Cited

U.S. PATENT DOCUMENTS 5,532,227   7/1996   Golub et al. ............................ 514/152

FOREIGN PATENT DOCUMENTS 9513805   5/1995   WIPO .
9631242   10/1996   WIPO .

OTHER PUBLICATIONS

Boyle PJ, Kempers, SF, O'Connor AM and Nagy RJ, "Brain glucose uptake and unawareness of hypoglycemia in patients with insulin–dependent diabetes mellitus," *New England J. Medicine* 333(26):1726–1731 (1995).

Brownlee M, Cerami A, and Vlassara H, "Advanced glycosylation end products in tissue and the biochemical basis of diabetic complications," *Seminars in Medicine of the Beth Israel Hospital, Boston*, 318(20):1315–1321 (1980).

Cerami A, Vlassara H, Brownlee M, "Role of advanced glycosylation products in complications of diabetes," *Diabetes Care*, 11(1):73–79 (1988).

Department of Health and Human Services, Public Health Service, Centers for Disease Control, National Center for Chronic Disease Prevention and Health Promotion, Division of Diabetes Translation, *The Prevention and Treatment of Complication of Diabetes Mellitus: A Guide for Primary Care Practitioners*, (1991) (copy obtained from Centers for Disease Control web site Dec. 4, 1996).

The Diabetes Control and Complications Trial Research Group, "The effect of intensive treatment of diabetes on the development and progression of long–term complications in insulin–dependent diabetes mellitus," *New England J. Medicine*, 329(14): 977–986 (1993).

Golub LM, Lee HM, Lehrer G, Nemiroff A, McNamara TF, Kaplan R, and Ramamurthy NS, "Minocycline reduces gingival collagenolytic activity during diabetes," *J. Periodontal Research*, 18:516–526 (1983).

Golub LM, Ramamurthy NS, Kaneko H, Sasaki T, Rifkin B, and McNamara TF, "Tetracycline administration prevents diabetes–induced osteopenia in the rat: initial observations," *Research Communications in Chemical Pathology and Pharmacology*, 68(1):27–40 (1990).

Grossi SG, Skrepcinski FB, DeCaro T, Zambon JJ, Cummins D, and Genco RJ, "Response to periodontal therapy in diabetes and smokers," *J. Periodontol*, 67(10):1094–1102 (1996).

Hamlin CR, Kohn RR, and Luschin JH, "Apparent accelerated aging of human collagen in diabetes mellitus," *Diabetes*, 24(10):902–904 (1975).

Ishii H, Jirousek MR, Koya D, Takagi C, Xia P, Clermont A, Bursell SE, Kern TS, Ballas LM, Heath WF, Stramm LE, Feener EP and King GL, "Amelioration of vascular dysfunctions in diabetic rats by an oral PKC β inhibitor," *Science*, 272:728–731 (1996).

Lewin DI, "Brain's adaptation to low blood sugar endangers diabetics," *J. NIH Research*, 8:38–39 (1996).

Makita Z, Radoff S, Rayfield EJ, Yang Z, Skolnik E, Delaney V, Friedman EA, Cerami A and Vlassara H, "Advanced glycosylation end products in patients with diabetic nephropathy", *New England J. Medicine* 836–842 (1991).

Yu Z, Ramamurthy NS, Leung M, Chang KM, McNamara TF and Golub LM, "Chemically–modified tetracycline normalizes collagen metabolism in diabetic rats: a dose–response study," *J. Periodontal Research*, 28:420–428 (1993).

Porte J Jr and Schwartz MW, "Diabetes complications: Why is glucose potentially toxic?," *Science*, 272:699–700 (1996).

Reiser KM, "Nonenzymatic glycation of collagen in aging and diabetes," __, 17–29 (1990).

Schneir M, Ramamurthy N, and Golub L, "Minocycline–treatment of diabetic rats normalizes skin collagen production and mass: possible causative mechanisms," *Matrix*, 10:112–123 (1990).

Windholz et al., *The Merck Index*, 10$^{th}$ Ed. (1983) pp. 723 & 724: abstract No. 4866. Insulin.

*Primary Examiner*—Kevin E. Weddington
*Attorney, Agent, or Firm*—Hoffmann & Baron, LLP

[57]  ABSTRACT

A method for treating diabetes in a mammal by moderately controlling blood glucose concentration in the mammal together with administering to the mammal an amount of a tetracycline compound effective to reduce complications associated with diabetic hyperglycemia. The method enables long term management of diabetes by avoiding the problems associated with tight control of blood glucose concentrations, i.e., hypoglycemia tolerance and seizures, while simultaneously avoiding the problems associated with conventional moderate control of blood glucose concentrations, i.e., pathological complications associated with hyperglycemia, such as nephropathy, retinopathy, etc. Blood glucose concentration can be controlled by moderate administration (e.g., fewer injections per day) of insulin or another glucose-modulating agent, while pathological complications characteristic of diabetic hyperglycemia are ameliorated through the activity of tetracycline compound, the latter preferably administered in an amount that is substantially non-antimicrobial.

39 Claims, No Drawings

THERAPEUTIC METHOD FOR MANAGEMENT OF DIABETES MELLITUS

This invention was made with Government support under Grant Nos. K 11 DE-00363 and R37 DE-03987 awarded by the National Institutes of Health through the National Institute of Dental Research. The Government has certain rights in the invention.

BACKGROUND OF THE INVENTION

The invention relates to a method of using tetracycline compounds in the treatment of diabetes. Specifically, the invention relates to a therapeutic method of using tetracyclines in managing patients suffering from pathological conditions associated with diabetes mellitus.

Diabetes mellitus (DM) is a complex chronic disorder of carbohydrate, fat, and protein metabolism that results primarily either from a partial or complete lack of insulin secretion by the beta cells of the pancreas or from defects in cellular insulin receptors. DM is the sixth leading cause of death from disease in the United States. According to the American Diabetes Association, approximately 12–14 million Americans have diabetes. It is estimated, however, that more than half of these people have yet to be formally diagnosed to have this disease.

Two types of diabetes are recognized. Type I diabetics are patients dependent upon exogenous insulin to prevent ketoacidosis. Accordingly, these patients are said to suffer from Insulin-Dependent Diabetes Mellitus (IDDM), previously known as juvenile-onset, brittle, or ketosis-prone diabetes. Type II diabetics are those with Non-Insulin-Dependent Diabetes Mellitus (NIDDM), and were previously designated as having maturity-onset, adult-onset, ketosis-resistant, or stable diabetes.

The pathological complications of diabetes are fundamentally related to hyperglycemia (Porte Jr et al. 1996). While presently not well understood, the mechanisms involved in these complications are beginning to be elucidated. For example, it appears that hyperglycemia can induce increased aldose reductase activity which affects sorbitol accumulation, depletes neural myoinositol, and alters Na-K ATPase activity. Hyperglycemia also increases diacylglycerol and $\beta_2$ protein kinase C activity, which in turn alters the contractility and hormone responsiveness of vascular smooth muscle, and alters endothelial cell permeability (Ishii et al. 1996). Moreover, hyperglycemia is associated with accelerated non-enzymatic glycosylation processes which activate endothelial and macrophage receptors for advanced glycosylation endproducts (AGEs), and alters lipoproteins as well as matrix and basement membrane proteins. Clearly, the consequences of glucose toxicity are globally distributed throughout the physiology of the diabetes patient.

Characteristically, the course of the disease is progressive, and includes polyuria, polyphagia, polydipsia, weight loss, hyperglycemia, and glycosuria. Numerous organ systems can be affected pathologically, including the eyes (resulting in retinopathy and cataract of the lens), kidneys (resulting in nephropathy), nervous system (resulting in neuropathy), circulatory system (resulting in angiopathy), teeth (resulting in periodontitis), bone (resulting in osteopenia), and skin. Diabetic retinopathy is one of the leading causes of blindness in the United States. Nephropathy leads to kidney failure, which can require dialysis, and is life-threatening. The goal of treatment is to reduce hypoglycemia, and to moderate or eliminate the effects of these pathologies. Typically, success is critically dependent on maintaining insulin-glucose homeostasis.

Currently, diabetes mellitus is managed by means of a controlled carbohydrate diet and daily insulin injections, or by hypoglycemic agents such as the short-acting agents acetohexamide, tolbutamide, tolazamide, and long-acting agents chlorpropamide, glipizide, and glyburide.

The Diabetes Control and Complications Trial (DCCT), a ten-year study completed in mid-1993, demonstrated that tight or "intensive" control of blood glucose levels-i.e., frequent self-monitoring of glucose levels and maintenance of these levels as close as possible to those in nondiabetics-significantly reduces diabetes-associated complications, such as retinopathy, nephropathy and neuropathy (DCCT Research Group 1993). As defined in the DCCT, "intensive" control meant that the diabetic patient followed a strict regimen, including controlling glucose tightly by three or more daily insulin injections or by means of an insulin pump. Intensive control was distinguished from a more moderate regimen termed "conventional" control, which included only one or two injections of insulin a day and less frequent monitoring of blood glucose concentration. The DCCT showed that the frequency of health complications was 40–75% lower for persons in the intensive control group than for those in the conventional treatment group (DCCT Research Group 1993). It has since become a central doctrine of diabetic management that the intensive control of hyperglycemia is critical to effective retardation or delay in the appearance or progression of the late complications of the disease.

Diabetic patients are taught to recognize the signs of impending hypoglycemia and insulin shock (e.g., headache, hunger, nervousness, irritability, diaphoresis, thready pulse, tremors and slurred speech). Hypoglycemia can be seen in both subsets of diabetics (IDDM and NIDDM) and is caused by either too much insulin or inadequate caloric intake (CDC Guide). However, it was also found in the DCCT that patients in the intensive treatment group more often suffered from seizures or coma or required another person's assistance to recover from hypoglycemia than did patients treated less intensively. The chief adverse complication associated with intensive therapy was 3-fold increase in the incidence of severe hypoglycemia, defined as the need for assistance from others, as compared to diabetics undertaking conventional therapy (DCCT Research Group 1993).

This observation is attributed to the unusual and interesting feature of the brain that, while like other organs systems in its reliance on blood glucose concentration for function, the brain differs from other organs in that it does not need insulin to utilize glucose. Boyle et al. (1995) have reported that hypoglycemia is likely to lead to a reversible, maladaptive central nervous system tolerance to subnormal plasma glucose concentrations. Specifically, certain autonomic portions of the brain adapt physiologically, learning to tolerate low blood glucose levels. By contrast, the rest of the brain, and in particular the cognitive portions, do not possess this capacity. Defective glucose counterregulation can occur even after only a single recent episode of hypoglycemia. Patients who experience repeated episodes of hypoglycemia often lose their capacity to recognize the symptoms typically associated with hypoglycemia or impending insulin shock, a condition called "hypoglycemia unawareness." Because the patient doesn't appreciate his or her own status, blood glucose levels can then fall so low that serious neurological problems ensue, including coma and seizure.

Thus, the danger in maintaining artificially a patient's blood glucose within the narrow, normal range-the essence of intensive control prescribed according to the DCCT—is that such regimens can induce recurrent low blood-glucose levels, raising the threat of seizure or a coma with little or no warning. Lewin (1996) has recognized that tight control of the blood glucose levels poses a difficult dilemma. Specifically, while tight control of blood glucose levels appears to be required to control hyperglycemia-associated pathology, in practice the patient often overcorrects, thereby inducing repeated episodes of hypoglycemia, giving rise to hypoglycemia unawareness.

Boyle et al. (1995) found that, because the body, and especially the brain, adapts to lower blood sugar levels, there is little margin between the blood glucose level at which hypoglycemic signs become perceptible and the level at which dangerous cognitive impairment occurs. Accordingly, patients with IDDM who use rigorous treatment regimens to maintain near-normal plasma glucose levels are at increased risk for seizures and comas. Boyle et al. conclude their article noting that their results would "challenge patients with IDDM and their physicians," due to the difficulty involved in achieving the tightest level of glycemic control (to minimize microvascular and other complications) while at the same time avoiding even a slight degree of hypoglycemia (to avoid central nervous system tolerance to subnormal glucose levels). However, Boyle et al. do not propose any specific therapeutic modality for meeting this challenge.

Porte Jr et al. (1996) have also commented on this tight-control dilemma. They point out that "[g]lucose is a molecule essential for life," but they emphasize "its concentration must be carefully controlled because of the powerful adverse effects of both too much and too little glucose." Porte Jr et al. conclude "the obstacles to the complete understanding of glucose toxicity and its prevention are formidable." There is a clear need for additional understanding of these interrelated physiological processes, as well as for new diabetes treatment regimens that avoid the problems that have so far plagued effective patient management.

Tetracyclines are a class of compounds that are particularly well known for their early and spectacular success as antibiotics. Such compounds as tetracycline, sporocycline, etc., are broad spectrum antibiotics, having utility against a wide variety of bacteria and other microbes. The parent compound, tetracycline, has the following general structure:

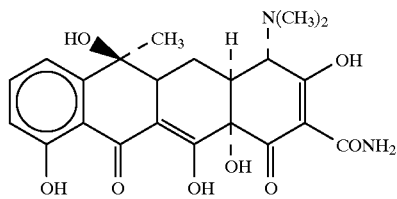

The numbering system for the multiple ring nucleus is as follows:

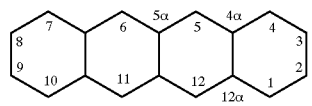

Tetracycline, as well as the 5-OH (terramycin) and 7-Cl (aureomycin) derivatives, exist in nature, and are all well known antibiotics. Semisynthetic derivatives such as the 7-dimethylamino derivative (minocycline), are also known antibiotics. The use of tetracycline antibiotics, while generally effective for treating infection, can lead to undesirable side effects. For example, the long-term administration of antibiotic tetracyclines can reduce or eliminate healthy flora, such as intestinal flora, and can lead to the production of antibiotic resistant organisms or the overgrowth of opportunistic yeast and fungi. These side-effects of long-term tetracycline therapy can be particularly disadvantageous to patients with diabetes because these patients tend to be abnormally highly susceptible to infection and impaired wound healing, which might at some juncture require antibiotic therapy to combat infection. Diabetes patients, in particular, tend to develop chronic yeast infections even without complications associated with antibiotic use.

Natural tetracyclines may be modified without losing their antibiotic properties, although certain elements of the structure must be retained to do so. Recently, however, a class of compounds has been defined that are structurally related to the antibiotic tetracyclines, but which have had their antibiotic activity substantially or completely extinguished by chemical modification. The modifications that may and may not be made to the basic tetracycline structure have been reviewed by Mitscher (1978). According to Mitscher, the modification at positions 5–9 of the tetracycline ring system can be made without causing the complete loss of antibiotic properties. However, changes to the basic structure of the ring system, or replacement of substituents at positions 1–4 or 10–12, generally lead to synthetic tetracyclines with substantially less, or essentially no, antimicrobial activity. For example, 4-de(dimethylamino)-tetracycline is commonly considered to be a non-antibacterial tetracycline. These compounds, known as chemically-modified tetracyclines (CMTs) have been found to possess a number of interesting properties, such as the inhibition of excessive collagenolytic activity both in vitro and in vivo. See, for example, Golub et al. (1991).

Tetracycline compounds have been observed to prevent or inhibit a variety of conditions, many of which are also recognized as diabetic complications. For example, tetracyclines inhibit non-enzymatic glycosylation of proteins. See, e.g., U.S. Pat. No. 5,532,227 to Golub et al., the entire disclosure of which is incorporated herein by reference. Tetracyclines, administered at both antimicrobial levels and at non-antimicrobial levels, have been known to play a role in reducing the activity of collagenase and other collagenolytic matrix metalloproteinases. Glycosylation and collagenolytic activity both may be related to a number of diabetic complications such as retinopathy, neuropathy, nephropathy, angiopathy, periodontitis, and impaired wound healing. Diabetics have connective tissue changes that can contribute to diabetic complications, such as reduced collagen solubility and decreased collagen synthesis. In diabetics, tetracyclines can prevent excessive collagen cross-linking (premature aging) and its associated complications, in addition to increasing collagen synthesis leading to an increase in newly synthesized, soluble uncross-linked collagen.

Tetracyclines have also been shown to reduce other pathophysiological complications characteristic of diabetes. For example, these compounds reduce or prevent proteinuria and albuminuria, related to nephropathy. It is also known that tetracyclines are capable of preventing cachexia or wasting in diabetic animals. Tetracyclines can inhibit abnormal lipid metabolism which has been associated with diabetic angiopathy and neuropathy. Moreover, it has been demonstrated that tetracyclines can inhibit nitric oxide synthetase (NOS), a potent natural vasodilator that is elevated in the presence of the effector cytokine, IL-1. Nitric oxide may also contribute to both diabetic nephropathy and angiopathy.

Applicants, however, are not aware of any evidence in the prior art disclosing or suggesting that tetracycline compounds could be of any use in modifying the most fundamental treatment modality for diabetes: the regulation of hyperglycemia by administration of insulin.

In view of the above considerations, it is clear that existing methods for controlling diabetes mellitus are limited in a number of ways. For example, the existing art does not provide efficient means for treating patients suffering from diabetes mellitus to avoid complications from either too much or too little blood glucose. Currently available treatment modalities are either too intrusive, e.g., insulin pumps, or require too much monitoring and intervention by the patient, e.g., tight control regimens, and yet they still fail to find safe passage between the Scylla of hypoglycemic neuropathology and the Charybdis of hyperglycemic tissue glycosylation and organ pathology.

Accordingly, it is one of the purposes of this invention to overcome the above limitations in the practice of medicine, by providing a method of treating patients suffering from diabetes mellitus that avoids the perils inherent in conventional treatment regimens.

SUMMARY OF THE INVENTION

It has now been discovered that these and other objectives can be achieved by the present invention, which provides a therapeutic method for treating a mammal suffering from diabetes mellitus.

In one embodiment, the invention is a therapeutic method for treating a mammal having diabetes mellitus, comprising:

a) administering a glucose modulating agent to the mammal using a regimen that maintains moderate control of average blood glucose concentration in the mammal; and b) administering a glycosylation-inhibiting agent to the mammal in an amount that inhibits development or progression of a pathological complication characteristic of hyperglycemia associated with diabetes mellitus in the mammal.

The glycosylation-inhibiting agent can be a tetracycline compound. Preferably, the tetracycline compound is administered in an amount that has substantially no antimicrobial activity. Preferred tetracycline compounds include, for example, 4-de(dimethylamino)-tetracycline (CMT-1), 6-demethyl-6-deoxy-4-de(dimethylamino)-tetracycline (CMT-3), 4-de(dimethylamino)-12α-deoxytetracycline (CMT-7), or 6-deoxy-5α-hydroxy-4-de(dimethylamino)-tetracycline (CMT-8).

Alternatively, the glycosylation-inhibiting agent can be aminoguanidine or other agent that inhibits glycosylation.

The method can include administering insulin as the glucose-modulating agent. In such cases, the administering regimen preferably comprises injecting insulin no more than an average of twice daily. The method can further comprise administering an adjuvant hypoglycemic agent to the mammal.

Alternatively, the glucose modulating agent can be a non-insulin hypoglycemic agent. The hypoglycemic agent can selected from among compounds such as sulfonyl ureas, thiazolidine diones, alpha-glucosidase inhibitors, and insulin-releasing agents, and the like.

In another embodiment, the invention is a method for treating a mammal having diabetes mellitus, comprising:

a) administering a glucose-modulating agent to the mammal using a regimen that substantially avoids inducing hypoglycemia tolerance in nervous tissue of the mammal; and b) administering a glycosylation-inhibiting agent to the mammal in an amount that inhibits development or progression of a pathological complication characteristic of diabetic hyperglycemia.

In the method, the glycosylation-inhibiting agent can be a tetracycline compound. The tetracycline compound is preferably administered in an amount that has substantially no antimicrobial activity. Preferably, the tetracycline compound is:

4-de(dimethylamino)-tetracycline (CMT-1),
6-demethyl-6-deoxy-4-de(dimethylamino)-tetracycline (CMT-3),
4-de(dimethylamino)-12α-deoxytetracycline (CMT-7), or
6-deoxy-5α-hydroxy-4-de(dimethylamino)-tetracycline (CMT-8).

Alternatively, the glycosylation-inhibiting agent can be aminoguanidine or other inhibitor of non-enzymatic glycosylation.

The glucose-modulating agent can be insulin. Preferably, the administering regimen comprises injecting insulin no more than an average of twice daily. The method can further comprise administering an adjuvant hypoglycemic agent to the mammal.

Alternatively, the glucose-modulating agent is a non-insulin hypoglycemic agent. Preferred hypoglycemic agents can be selected from among compounds such as sulfonyl ureas, thiazolidine diones, alpha-glucosidase inhibitors, and insulin-releasing agents, and the like.

In another embodiment, the invention is a method of reducing the development or progression of a diabetes-associated pathological complication in a mammal, comprising administering to the mammal a glycosylation-inhibiting agent in an amount that inhibits the development or progression of the pathological complication, and maintaining plasma glucose concentrations in the mammal in a moderate range while limiting central nervous system tolerance to hypoglycemia.

Again, the glycosylation-inhibiting agent can be a tetracycline. The tetracycline compound is preferably administered in an amount that has substantially no antimicrobial activity. Preferred modified tetracycline compounds include, for example:

4-de(dimethylamino)-tetracycline (CMT-1),
6-demethyl-6-deoxy-4-de(dimethylamino)-tetracycline (CMT-3),
4-de(dimethylamino)-12α-deoxytetracycline (CMT-7), or
6-deoxy-5α-hydroxy-4-de(dimethylamino)-tetracycline (CMT-8).

Alternatively, the glycosylation-inhibiting agent can be aminoguanidine or other functionally similar compound.

The maintaining of the blood glucose concentration can comprise administering insulin to the mammal. Preferably, the method comprises injecting insulin no more than an average of about twice daily. The method can further comprise administering an adjuvant hypoglycemic agent to the mammal.

Alternatively, the maintaining of the blood glucose concentration comprises administering a non-insulin hypoglycemic agent to the mammal. Preferred hypoglycemic agents include, for example, sulfonyl ureas, thiazolidine diones, alpha-glucosidase inhibitors, and insulin-releasing agents, and the like.

In another embodiment, the invention is a method of treating a mammal having a diabetes condition, comprising:

administering a glycosylation-inhibiting agent to the mammal in an amount effective to inhibit hyperglycemia-associated pathological complications of the diabetes condition;

controlling moderately blood glucose concentrations in the mammal by administering a glucose-modulating agent to the mammal.

Preferably, the glycosylation-inhibiting agent is a tetracycline compound. The tetracycline compound is administered in an amount that has substantially no antimicrobial activity. Commercially available antimicrobial tetracyclines can be given in sub-antimicrobial doses, but tetracyclines modified to have reduced antimicrobial activity can be given in larger doses. Preferred tetracycline compounds include, for example:

4-de(dimethylamino)-tetracycline (CMT-1),
6-demethyl-6-deoxy-4-de(dimethylamino)-tetracycline (CMT-3),
4-de(dimethylamino)-12α-deoxytetracycline (CMT-7), or
6-deoxy-5α-hydroxy-4-de(dimethylamino)-tetracycline (CMT-8).

Alternatively, the glycosylation-inhibiting agent is aminoguanidine or other inhibitor of glycosylation.

A preferred glucose-modulating agent is insulin, and the method preferably comprises administering insulin to the mammal in an amount or a frequency which is significantly lower than the amount or frequency normally required for mitigation of the hyperglycemia-associated pathological complications in the mammal. Thus, the method can comprise injecting insulin no more than an average of about twice daily. The method can further comprise administering an adjuvant hypoglycemic agent to the mammal.

Alternatively, the maintaining of the blood glucose concentration comprises administering a non-insulin hypoglycemic agent to the mammal. Suitable hypoglycemic agents include, for example, sulfonyl ureas, thiazolidine diones, alpha-glucosidase inhibitors, and insulin-releasing agents, and the like.

Preferably, the maintaining of the blood glucose concentration in the method of the invention is achieved by means of a therapeutic regimen comprising administering insulin to the Type I diabetic mammal or insulin or a hypoglycemic agent to the Type II diabetic mammal.

Thus, the method of the invention permits the moderation of treatment in diabetic patients by administering a tetracycline compound that can ameliorate or reduce the pathological complications that might otherwise be associated with hyperglycemia. The method, therefore, substantially reduces the likelihood of, and the problems associated with, recurrent hypoglycemic episodes characteristic of tight or intensive blood glucose control regimens.

These and other advantages of the present invention will be appreciated from the detailed description and examples that are set forth herein. The detailed description and examples enhance the understanding of the invention, but are not intended to limit the scope of the invention.

DETAILED DESCRIPTION OF THE PREFERRED EMBODIMENTS

The present invention is directed to a method for managing patients suffering from diabetes mellitus so as to overcome the problems inherent in prior art methods. The method of the invention includes treating a mammal having diabetes mellitus by administering a glucose-modulating agent (preferably administering insulin or a non-insulin hypoglycemic compound) to the mammal, and administering a glycosylation-inhibiting agent (such as a tetracycline compound) to the mammal.

Applicants believe that diabetic patients need not be placed at risk for potentially brain-damaging or life-threatening seizure or coma as a result of current therapeutic regimens. In contrast to the conventional understanding of this disease, the goal of treatment should not be to maintain insulin-glucose homeostasis so tightly that it places the patient at risk of repeated episodes of hypoglycemia. Instead, if the balance is tipped towards mild hyperglycemia while still protecting the patient from the long-term complications associated with elevated blood glucose, then it becomes possible to prevent the brain's adaptation to low blood glucose. It is this adaptation that endangers those diabetics who have historically been required to maintain rigorous glucose control. The approach described herein constitutes a radical, fundamental shift in the concept of diabetes treatment.

According to the method of the invention, patients deliberately maintained in a mildly hyperglycemic posture can be protected from potential long-term complications by treating them with a glycosylation-inhibiting agent, preferably a tetracycline compound, in an amount that is effective to offset or counteract long-term hyperglycemic complications. While antimicrobial amounts of a tetracycline compound can be employed, it is preferred to use an amount of a modified compound that has substantially no antimicrobial activity. Chemically modified tetracyclines are known that, unlike the parent compound tetracycline, have substantially no antimicrobial capabilities. This is important when considering long-term treatment in diabetics who have a tendency to develop thrush or Candida infections, which antibiotic treatment can exacerbate. Moreover, long-term treatment with antimicrobial tetracyclines could result in the emergence of tetracycline- or pan-antibiotic-resistant bacteria that would be life-threatening in patients with diabetes mellitus who are already excessively susceptible to infections because of impaired host responses. Alternatively, a sub-antimicrobial dose of a commercially available antimicrobial tetracycline (e.g., doxycycline) could also be used.

In addition to treatment with a tetracycline (preferably non-antibacterial amounts thereof) and moderate amounts of the primary glucose-modulating agent, e.g., insulin, diabetic patients may be further moderately controlled by providing a diet limited in carbohydrates, or by administering an adjuvant hypoglycemic agent. Suitable adjuvant hypoglycemic agents (typically oral) are known in the art, such as the short-acting agents acetohexamide, tolbutamide, tolazamide, and long-acting agents chlorpropamide, glipizide, and glyburide. Preferably the adjuvant agent is an agent that increases insulin receptors in the mammal being treated.

The method of the invention, therefore, allows for the patient to lead a more normal life wherein:

1) carbohydrate dietary constraints are not as stringent;
2) the number (IDDM) or need (NIDDM) for injections of insulin (or other agent) is reduced;
3) frequent self-monitoring is not as critical;
4) the risk of complications from hyperglycemia is reduced; and
5) the risk of complications from hypoglycemia such as coma or seizure related to hypoglycemia unawareness is reduced.

The treatment of diabetes by the method of the invention can decrease the likelihood of pathological complications that lead to premature death. Preferably, the treatment can be used to actually improve the patient's quality of life.

The therapeutic regimen described herein will require some adjustment by treating physicians. The physicians will find that the method of the invention enables higher thresholds for acceptable blood glucose and glycosylated hemoglobin levels (a measure of long-term diabetic control). Glycosylated serum protein (GSP) levels, e.g., levels of glycosylated albumin, which are currently used to measure short-term control, could be meaningless for determining insulin-glucose homeostasis since tetracyclines inhibit non-enzymatic glycosylation of these serum proteins. However, GSP levels can instead be used as a diagnostic indicator of the efficacy of the tetracycline regimen for reducing non-enzymatic glycosylation (or reducing generation of advanced glycosylation endproducts) in the diabetic.

Beyond the benefits to the patient as described herein, a definite benefit accrues to physicians as well, in that the method of the invention decreases the likelihood of prescribing doses of insulin that could place patients, especially those who do not carefully monitor their blood glucose levels, at a higher risk of shock or coma from hypoglycemia. Treatment according to the invention would thereby make the physician's management of diabetic patients far less complicated.

The method of the invention permits amelioration or elimination of a pathological complication characteristic of diabetes mellitus or diabetes-associated hyperglycemia. Ideally, the method permits amelioration of all of the pathology associated with diabetes, but the practitioner will appreciate that the responses of individuals to specific treatment regimens can be variable or idiosyncratic. Thus, the method can be used to moderate or ameliorate one or more of the pathological complications characteristic of or associated with diabetes or diabetic hyperglycemia.

The conditions treatable by means of the present invention occur in mammals. Human diabetics are, of course, the most important mammals treatable according to the method of the invention, but the method can be practiced for the benefit of other mammals, including, for example, pet animals such as dogs and cats, laboratory animals such as rats and mice, as well as farm animals such as horses and cows. The term "patient" is used herein to emphasize the importance of the invention in the treatment of humans, but this usage should not be understood to limit the invention to the treatment of humans to the exclusion of other mammalian subjects.

Numerous pathological complications have been identified as being occasionally or commonly present in patients having been diagnosed to have diabetes. Such conditions are, therefore, said to be characteristic of diabetes or associated with diabetes. These pathological complications are treatable through the method of the invention. The pathological complications capable of treatment in this way include, for example, increased leatheriness of skin, decreased lung elasticity, increased arterial wall stiffness and angiopathy, limitation of joint movement, impaired wound healing, nephropathy resulting in proteinuria, peripheral and autonomic neuropathies, background and proliferative retinopathies, cataract of the lens of the eye, periodontal disease, etc. Many of these conditions develop only over the long term, after years of diabetic hyperglycemia. The ability to prevent or ameliorate these conditions, whether localized or systemic, through the method of the invention, while still avoiding problems associated with hypoglycemia tolerance, constitutes a major advance in the management of diabetic patients.

The diagnosis of diabetes is dependent upon establishing a pattern of hyperglycemia, i.e., an elevated glucose concentration in the blood. The skilled clinician will appreciate that blood (plasma) glucose concentrations constantly fluctuate, especially in response to meals and physiological stresses (e.g., exercise). Normal glucose concentrations in humans range between about 50 mg/dL (2.8 mM) and about 90 mg/dL (5.0 mM) when measured in whole blood or plasma, and between about 70 mg/dL (3.9 mM) and about 105 mg/dL (5.9 mM) when measured in serum.

Levels outside these ranges can occur, relatively infrequently in normal individuals, but more frequently in diabetics and those with incipient diabetes. For example, diabetics can present with random plasma glucose concentrations of about 200 mg/dL (11.2 mM) or more, and fasting plasma glucose concentrations of about 140 mg/dL (7.8 mM) or more. Serum glucose concentrations of about 180 mg/dL (10 mM) or higher are considered significantly high, being indicative of diabetic hyperglycemia.

On the other hand, serum glucose levels as low as about 75 mg/dL (4.2 mM) begin to affect sympathoadrenal responses, leading to an increase in sympathetic tone that is a fundamental indicator to the patient of hypoglycemia. Levels below about 70 mg/dL (3.9 mM), and more significantly, below 60 mg/dL (3.6 mM) are considered to be substantially hypoglycemic. But normal humans can adapt to tolerate plasma glucose concentrations as low as about 45 mg/dL (2.5 mM) (Boyle et al. 1996).

It is generally understood that, unfortunately, there is presently no precise value of blood glucose concentration that can be employed to definitively establish the presence of diabetes. Moreover, certain individuals may be more tolerant of higher blood glucose levels than others, and it is difficult to definitively establish whether a particular glucose level measured on a particular day is unacceptably high for the individual in question. Therefore, treatment for diabetes generally focuses on maintaining average glucose levels in a relatively narrow range defined to be acceptable for the given patient. This is often measured indirectly by determining the levels of glycosylated hemoglobin, which permits the practitioner to estimate the patient's blood glucose history over the preceding six to eight weeks.

One measure used as an indicator of diabetes and impaired glucose tolerance is the glucose tolerance test, which measures blood glucose levels over a two hour period under standardized testing conditions. Impaired glucose tolerance is generally diagnosed if the blood glucose level measured during a glucose tolerance test is in the range of 140 mg/dL (7.84 mM) to 199 mg/dL (11.1 mM). Diabetes is generally diagnosed if the measured blood glucose level is 200 mg/dL (11.2 mM) or higher. But, as physiological status fluctuates continually, no single glucose tolerance test is definitive, and treatment for reducing of blood glucose levels need not be predicated solely on the results of such testing.

The DCCT observed that the intensive control regimen managed to reduce average blood glucose concentrations to about 40 percent above normal average levels, i.e., about 155 mg/dL (8.7 mM) in the intensively controlled diabetics as compared to a normal level, which was measured as about 110 mg/dL (6.2 mM). Accordingly, a moderate control regimen may be defined as a regimen that permits average blood glucose concentration in a human patient to exceed about 40% above the normal level. This differential can vary broadly across species, with rats having a normal blood glucose level of about 200 mg/dL (11.2 mM), and being capable of tolerating glucose levels of about 500 mg/dL (28 mM) or more without substantial morbidity or mortality.

However, because the conventionally acceptable range of glucose concentrations is so narrow, the patient in an intensive treatment regimen is typically required to monitor his or her own blood glucose concentration three or more times per day, and to self-inject insulin three or more times per day. In patients suffering from particularly unstable diabetes, use of an insulin pump for continuous sub-cutaneous infusion may be indicated. However, because pumps are an especially onerous burden on the patient, they are generally not a first choice among treatment modalities, and multiple injection protocols are preferred. Under the intensive multiple injection approach, it is typical for the patient to test his or her blood glucose (alternatively urinalysis) before each meal, calculate an appropriate dosage of an intermediate and/or rapid-acting insulin, and self-administer the insulin.

It is one of the advantages of the present invention that the method enables the subject to tolerate mild hyperglycemia, and the range of acceptable glucose concentrations for the subject becomes significantly larger. As a result, patients are not required to monitor glucose concentration as closely, and insulin injections can be limited, e.g., fewer than three injections per day on average, often with the use of an intermediate or slow-acting insulin. This moderation of the therapeutic regimen is much easier for the patient to tolerate, thereby facilitating compliance. But not only does the method of the invention enable a patient to escape the rigors of the intensive treatment regimen, the invention further permits other patients undertaking a conventional or more moderate protocols to further reduce the burdens associated with such methods, e.g., by reducing insulin injections, blood glucose determinations, etc.

Thus, the invention enables the individual to avoid the rigors of intensive control protocols. Intensive regimens, as used herein, is substantially consistent with the definition of intensive therapy employed in the DCCT (DCCT Research Group 1993). Specifically, "intensive control" means administering insulin three or more times daily by injection or an external pump, adjusting insulin dosage according to the results of self-monitoring of blood glucose performed at least four times daily, dietary intake and anticipated exercise. The goals of intensive therapy include preprandial blood glucose concentrations between 70 and 120 mg/dL (3.9 and 6.7 mM), postprandial blood glucose concentrations of less than 180 mg/dL (10 mM), a weekly 3-a.m. measurement greater than 65 mg/dL (3.6 mM), and hemoglobin $A_{1c}$ (glycosylated hemoglobin), measured monthly, within the normal range (less than 6.05%). Patients undergoing intensive therapy are required to visit their physician once a month, and are contacted more frequently by telephone to review and adjust their regimens.

By contrast, a "moderate diabetes treatment regimen" or "moderate control" can be defined as a regimen that is significantly less onerous for the patient to undertake on a long-term basis. Specifically, a moderate regimen can be defined as a regimen that reduces the amount and/or frequency of insulin administration significantly below that otherwise required for the patient. According to this definition, a moderate regimen requires an average of less than three, preferably about two, more preferably about one, and still more preferably less than one, insulin injections daily.

Alternatively, a moderate regimen can be defined as a regimen that significantly reduces the average daily number of blood glucose determinations to fewer than four, preferably about three, more preferably about two, and still more preferably, about one per day.

A moderate regimen can also be defined as a regimen that enables the patient to avoid adjusting insulin dosage, and accordingly reduces the requirement for close attention to dietary intake and anticipation of exercise.

Furthermore, a moderate regimen can be defined as a regimen that permits preprandial or postprandial blood glucose concentrations above or below the range specified for intensive control, elimination of 3-a.m. blood glucose measurements, or glycosylated hemoglobin measurements higher than 6.05%. Preferably, a moderate regimen defined in this way will include at least two of these significant parameter changes, more preferably at least three, and most preferably all four of these significant parameter changes.

Of course, each treatment regimen is designed by the physician to meet the individual's personal needs and abilities. Accordingly, different regimens can each qualify "moderate" as the term is employed herein, if they each differ significantly from the intensive control regimen as defined above, and satisfy at least one, preferably at least two, and more preferably at least three of the definitions of moderate control provided above.

The method of the invention includes a coordinated therapeutic regimen comprising the administration of a glucose-modulating agent and the administration of a glycosylation-inhibiting agent.

By "glucose-modulating agent" is meant any compound or combination of compounds that has the effect of improving the physiological homeostatic regulation of glucose metabolism. A preferred glucose-modulating agent is insulin, which is required for treating Type I diabetic mammals. Other preferred glucose-modulating agents include non-insulin hypoglycemic agents, which can be substituted for insulin in treating Type H diabetic mammals.

If the desired glucose-modulating agent is insulin, the insulin can be any form of insulin capable of use in the mammal being treated. Thus, insulin, including homologs and derivatives thereof, from natural, synthetic, semi-synthetic, and recombinant sources, is suitable for use. Slow-, intermediate-, and rapid-acting forms of insulin can be used. Non-peptide insulin receptor agonists can be employed as described in the art. The term "insulin" is used herein to refer to any of the above compounds or any compound that enables glucose uptake or utilization by cells through interaction with insulin receptors on cell surfaces.

If the desired glucose-modulating agent is a non-insulin hypoglycemic agent, then any such hypoglycemic agent can be used. Suitable hypoglycemic agents include those that increase insulin receptors in the mammal being treated, those that stimulate insulin secretion from the beta cells of pancreatic islet tissue, as well as those that act to modulate glucose metabolism by other physiological mechanisms. Accordingly, acceptable hypoglycemic agents include:

sulfonyl ureas, such as glibenclamide, gliclazide, glipizide (e.g., GLUCOTROL®), glyburide (e.g., DIAβETA® and MICRONASE®), chlorpropamide (e.g., DIABINESE®), tolbutamide (e.g., ORINASE®), tolazamide (e.g.,TOLINASE®), acetohexamide, and glimopride;

thiazolidine diones, such as troglitazone and ploglitazone;

alpha-glucosidase inhibitors, such as acarbose and miglitol;

3rd-generation insulin-releasing agents, such as KAD 1220, etoxomir, and repaglinide;

and the like. The hypoglycemic agent can be a short-acting hypoglycemic agent or a long-acting hypoglycemic agent. Hypoglycemic agents capable of oral administration are also preferred.

The administration of the glucose-modulating agent is accomplished by any technique adapted for use in the mammal being treated. In humans, the typical administration route for insulin is subcutaneous injection, in which several injections are made over the course of a 24 hour period. It is preferred to require fewer injections if possible, particularly two or fewer per day. The artisan understands that fewer injections generally require the use of slower-acting forms of insulin. The skilled artisan also recognizes that insulin administration regimens typically must be tailored to accommodate the needs of the patient. Accordingly, oral administration of insulin would be highly preferred. Also preferred is implantation of pancreatic islet cells using techniques to prevent their rejection. Several non-insulin hypoglycemic agents are available for oral administration.

By "glycosylation-inhibiting agent" is meant any agent that is effective to inhibit or reduce the rate of non-enzymatic glycosylation in the mammal. Tetracycline compounds are preferred for this inhibition of glycosylation, but other agents having similar functional efficacy can be used, e.g., aminoguanidine.

The tetracycline compound used in the method of the invention may be any tetracycline compound, from those that have potent antibiotic activity to those lacking any substantial antimicrobial activity. However, it is preferred that the tetracycline compound be administered in an amount that has substantially no antimicrobial activity, but that is effective for reducing a pathological complication associated with diabetic hyperglycemia. The method can, therefore, take advantage of tetracycline compounds that have been chemically modified to reduce or eliminate their antimicrobial properties. The use of such chemically-modified tetracyclines (CMTs) is preferred in the present invention since they can be used at higher levels than antimicrobial tetracyclines, while avoiding the disadvantages associated with antimicrobial activity as described elsewhere herein. However, sub-antimicrobial doses of typically antibacterial tetracyclines (e.g., doxycycline) can also be given according to the invention.

Preferred chemically-modified tetracyclines include those that lack the dimethylamino group at position 4 of the ring structure. This modification may be combined with other modifications to render the compounds suitable for use. Such chemically-modified tetracyclines include, for example, 4-de(dimethylamino)-tetracycline (CMT-1), 6-demethyl-6-deoxy-4-de(dimethylamino)-tetracycline (CMT-3), 4-de(dimethylamino)-7-chlorotetracycline (CMT-4), tetracycline pyrazole (CMT-5), 4-hydroxy-4-de (dimethylamino)-tetracycline (CMT-6), 4-de (dimethylamino)-12α-deoxytetracycline (CMT-7), 6-deoxy-5α-hydroxy-4-de(dimethylamino)-tetracycline (CMT-8), 4-de(dimethylamino)-12α-deoxyanhydrotetracycline (CMT-9), 4-de(dimethylamino)minocycline (CMT-10), 4-de (dimethylamino)-5-oxytetracycline, 5α,6-anhydro-4-hydroxy-4-de(dimethylamino)-tetracycline, 4-de (dimethylamino)-11-hydroxy-12α-deoxytetracycline, 1 2α-deoxy-4-deoxy-4-de(dimethylamino)-tetracycline, 12α, 4α-anhydro-4-de(dimethylamino)-tetracycline, and 7-dimethylamino-6-demethyl-6-deoxy-4-de (dimethylamino)-tetracycline. Also, tetracyclines modified at the 2 carbon position to produce a nitrile, e.g., tetracyclinonitrile (CMT-2), are useful as non-antibacterial tetracyclines.

Further examples of tetracyclines modified for reduced antimicrobial activity include 6-α-benzylthiomethylenetetracycline, the mono-N-alkylated amide of tetracycline, 6-fluoro-6-demethyltetracycline, or 11α-chlorotetracycline.

Particularly preferred tetracyclines include CMT-1, CMT-3, CMT-7, and CMT-8.

Preferred compounds having substantial antimicrobial activity include, for example, tetracycline, doxycycline, and minocycline and other well known tetracycline antibiotics, especially those already approved for use in humans.

The tetracycline compounds useful according to the method of the invention appear to exhibit their beneficial effect in a dose-dependent manner. Thus, within broad limits, administration of larger quantities of a tetracycline compound is typically more effective than is administration of a smaller amount. Moreover, efficacy is observed at dosages below the level at which toxicity is seen.

The amount of the tetracycline compound used according to the invention is an amount that is effective to offset or eliminate a hyperglycemia-associated pathological complication, preferably while not being effectively antimicrobial. An amount of a tetracycline compound is effective for use according to the invention if it is sufficient to significantly limit a pathological complication associated with blood glucose levels above the normal range found in the subject species.

The maximal dosage for a subject is the highest dosage that does not cause undesirable or intolerable side effects. For example, the tetracycline compound can be administered in an amount of from about 0.1 mg/kg/day to about 30 mg/kg/day, and preferably from about 1 mg/kg/day to about 18 mg/kg/day. For the purpose of the present invention, side effects include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field to consider standard pharmacokinetic criteria, including parameters of drug bioavailability such as serum half-life ($t_{1/2}$), and other parameters. Thus, the present invention includes, without limitation, dosages that are effective to achieve the described phenomena.

The preferred pharmaceutical composition for use in the method of the invention comprises a combination of the tetracycline compound in a suitable pharmaceutical carrier or excipient as understood by practitioners in the art. The means of delivery of the tetracycline compound with the pharmaceutical carrier may be in the form of a capsule, compressed tablet, pill, solution, or suspension suitable for administration to the subject. It is contemplated that compositions be included which are formulated with carriers suitable for administration orally, topically, by injection, or by other means. Time-release or controlled-delivery administration may be employed.

The practitioner understands that compliance with any pharmaceutical protocol is dependent upon whether the administration technique is subjectively acceptable to the patient. Conventional insulin treatment by multiple daily injections is too onerous a burden for many patients. Such intensive or tight glucose control is contraindicated for these patients. Accordingly, the method of the invention is deemed to be beneficial in particular cases if the administration of the glycosylation-inhibiting agent does not diminish compliance by the patient. Oral administration is, therefore, a preferred administration route, and tetracyclines suitable for systemic absorption through oral or enteric routes are known. Alternatively, the glycosylation-inhibiting agent can be administered by subcutaneous injection using a technique similar to that used to administer insulin, and to which the patient is previously accustomed. Indeed, the formulation of compositions comprising insulin in admixture with a tetracycline compound is contemplated as an embodiment of the present invention.

Recently, new information has been forthcoming about methods and compositions for the oral administration of insulin. Formulations can be prepared through which insulin and a tetracycline can be delivered orally. Oral insulin formulations can be used in conjunction with or combined with oral tetracycline formulations.

The invention finds particular utility in the treatment of patients suffering from insulin-dependent diabetes mellitus and having a history of episodic unawareness of hypoglycemia. In this case, the method of the invention can be used to reduce the amount or frequency of insulin administration below that which the patient normally employs, while administering to the patient an amount of a tetracycline compound sufficient to inhibit one or more pathological complications characteristic of hyperglycemia. The limitation of the amount or frequency of insulin administration allows the blood glucose level in such patients to fluctuate more than would generally be considered desirable, e.g., an average blood glucose level of about 40% or more above normal average levels. Nonetheless, a useful balance is struck between limiting neurological complications from hypoglycemic episodes associated with tight glucose control and the pathological complications associated with hyperglycemia.

The method finds further utility in treating a patient having insulin-dependent diabetes mellitus and insulin-associated abnormal central nervous system tolerance to subnormal plasma glucose concentration. In such cases, the method would comprise administering insulin (or a non-insulin hypoglycemic agent) in a "moderate" amount or frequency, i.e., an amount or frequency sufficient to inhibit abnormal central nervous system tolerance to subnormal plasma glucose concentration, while administering a glycosylation-inhibiting agent in an amount that is sufficient to minimize a pathological complication characteristic of supranormal plasma glucose concentrations. "Moderate control" of blood glucose concentration is considered to be a level of control of such concentration through insulin administration (with or without adjuvant treatment methods) that substantially avoids the induction of hypoglycemia unawareness in the patient.

Thus, the method is useful for reducing hypoglycemia-associated neurological complications in a mammal suffering from insulin-dependent diabetes mellitus or non-insulin-dependent diabetes mellitus. In this situation, the method would comprise administering a glucose-modulating agent such as insulin to the mammal using a regimen that allows mild hyperglycemia and that reduces hypoglycemia-associated neurological complications, and administering a tetracycline compound to the mammal in an amount that is effective to inhibit development or progression of one or more pathological complications characteristic of hyperglycemia associated with diabetes in the mammal.

In another embodiment, the invention is a therapeutic method for treating a mammal having diabetes mellitus, comprising:

a) administering a non-insulin hypoglycemic agent to the mammal using a regimen that maintains moderate control of average blood glucose concentration in the mammal; and b) administering a glycosylation-inhibiting agent to the mammal in an amount that inhibits development or progression in the mammal of a pathological complication characteristic of diabetes mellitus. Suitable non-insulin hypoglycemic agents (typically oral) are known in the art and are mentioned hereinabove, such as the short-acting agents acetohexamide, tolbutamide, tolazamide, and long-acting agents chlorpropamide, glipizide, and glyburide.

The skilled artisan will appreciate the flexibility in treatment regimens that is provided by the method of the invention, and will also appreciate the need to adjust dosage and treatment protocols to accommodate the idiosyncrasies of individual patients. The method is capable of implementation in numerous specific treatment regimens, either alone or in combination with other treatments for other and related conditions that may occur in some patients.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications, mentioned in the foregoing specification, are incorporated herein by reference for all that they disclose:

Boyle, P J, S F Kempers, AM O'Connor, and R J Nagy, "Brain glucose uptake and unawareness of hypoglycemia in patients with insulin-dependent diabetes mellitus," New Engl. J Med. 333(26):1726–1731 (1995).

Centers for Disease Control and Prevention, The Prevention and Treatment of Complications of Diabetes: A Guide for Primary Care Practitioners, National Center for Chronic Disease and Health Promotion, Division of Diabetes Translation (1991) [referred to in the text as "CDC Guide"].

The Diabetes Control and Complications Trial Research Group, "The effect of intensive treatment of diabetes on the development and progression of long-term complications in insulin-dependent diabetes mellitus," N. Engl. J Med. 329:977–986 (1993).

Golub, L M, N S Ramamurthy, T F McNamara, R A Greenwald, and B R Rifkin, "Tetracyclines inhibit connective tissue breakdown: New therapeutic implications for an old family of drugs," Crit. Rev. in Oral Biol. and Med. 2(2):297–322 (1991).

Ishii, H, M R Jirousek, D Koya, C Takagi, P Xia, A Clermont, S-E Bursell, T S Kern, L M Ballas, W F Heath, L E Stramm, E P Feener, and G L King, "Amelioration of vascular dysfunction in diabetic rats by an oral PKCβ inhibitor," Science 272:728–31 (1996).

Lewin, D L, "Brain's adaptation to low blood sugar endangers diabetics," J NIH Res. 8 (March):38–39 (1996)

Mitscher, L A, The Chemistry of the Tetracycline Antibiotics, Ch. 6, Marcel Dekker, New York (1978).

Porte Jr, D, and M W Schwartz, "Diabetes complications: Why is glucose potentially toxic?," Science 272:699–70 (1996).

What is claimed is:

1. A therapeutic method for treating a mammal having diabetes mellitus, comprising:

a) administering a glucose-modulating agent to the mammal using a regimen that maintains moderate control of average blood glucose concentration in the mammal; and b) administering a glycosylation-inhibiting agent to the mammal in an amount that inhibits development or progression of a pathological complication characteristic of diabetes mellitus in the mammal.

2. A method according to claim 1, wherein the glycosylation-inhibiting agent is a tetracycline compound.

3. A method according to claim 2, wherein the tetracycline compound is administered in an amount that has substantially no antimicrobial activity.

4. A method according to claim 2, wherein the tetracycline compound is:

4-de(dimethylamino)-tetracycline (CMT-1), 6-demethyl-6-deoxy-4-de(dimethylamino)-tetracycline (CMT-3), 4-de(dimethylamino)-12α-deoxytetracycline (CMT-7), or 6-deoxy-5α-hydroxy-4-de(dimethylamino)-tetracycline (CMT-8).

5. A method according to claim 1, wherein the glycosylation-inhibiting agent is aminoguanidine.

6. A method according to claim 1, wherein the glucose-modulating agent is insulin.

7. A method according to claim 6, wherein the administering regimen comprises injecting insulin no more than an average of twice daily.

8. A method according to claim 6, wherein the method further comprises administering an adjuvant hypoglycemic agent to the mammal.

9. A method according to claim 1, wherein the glucose-modulating agent is a non-insulin hypoglycemic agent.

10. A method according to claim 9, wherein the hypoglycemic agent is selected from the group consisting of sulfonyl ureas, thiazolidine diones, alpha-glucosidase inhibitors, and insulin-releasing agents.

11. A method for treating a mammal having diabetes mellitus, comprising:

a) administering a glucose-modulating agent to the mammal using a regimen that substantially avoids inducing hypoglycemia tolerance in nervous tissue of the mammal; and b) administering a glycosylation-inhibiting agent to the mammal in an amount that inhibits development or progression of a pathological complication characteristic of diabetic hyperglycemia.

12. A method according to claim 11, wherein the glycosylation-inhibiting agent is a tetracycline compound.

13. A method according to claim 12, wherein the tetracycline compound is administered in an amount that has substantially no antimicrobial activity.

14. A method according to claim 12, wherein the tetracycline compound is:

4-de(dimethylamino)-tetracycline (CMT-1), 6-demethyl-6-deoxy-4-de(dimethylamino)-tetracycline (CMT-3), 4-de(dimethylamino)-12α-deoxytetracycline (CMT-7), or 6-deoxy-5α-hydroxy-4-de(dimethylamino)-tetracycline (CMT-8).

15. A method according to claim 11, wherein the glucose-modulating agent is insulin.

16. A method according to claim 15, wherein the administering regimen comprises injecting insulin no more than an average of twice daily.

17. A method according to claim 11, wherein the method further comprises administering an adjuvant hypoglycemic agent to the mammal.

18. A method according to claim 11, wherein the glucose-modulating agent is a non-insulin hypoglycemic agent.

19. A method according to claim 18, wherein the hypoglycemic agent is selected from the group consisting of sulfonyl ureas, thiazolidine diones, alpha-glucosidase inhibitors, and insulin-releasing agents.

20. A method of reducing the development or progression of a diabetes-associated pathological complication in a mammal, comprising administering to the mammal a glycosylation-inhibiting agent in an amount that inhibits the development or progression of the pathological complication, and maintaining plasma glucose concentrations in the mammal in a moderate range while limiting central nervous system tolerance to hypoglycemia.

21. A method according to claim 20, wherein the glycosylation-inhibiting agent is a tetracycline compound.

22. A method according to claim 21, wherein the tetracycline compound is administered in an amount that has substantially no antimicrobial activity.

23. A method according to claim 21, wherein the tetracycline compound is:

4-de(dimethylamino)-tetracycline (CMT-1), 6-demethyl-6-deoxy-4-de(dimethylamino)-tetracycline (CMT-3), 4-de(dimethylamino)-12α-deoxytetracycline (CMT-7), or 6-deoxy-5α-hydroxy-4-de(dimethylamino)-tetracycline (CMT-8).

24. A method according to claim 20, wherein the maintaining of the blood glucose concentration comprises administering insulin to the mammal.

25. A method according to claim 24, wherein the method comprises injecting insulin no more than an average of about twice daily.

26. A method according to claim 24, wherein the method further comprises administering an adjuvant hypoglycemic agent to the mammal.

27. A method according to claim 20, wherein the maintaining of the blood glucose concentration comprises administering a non-insulin hypoglycemic agent to the mammal.

28. A method according to claim 27, wherein the hypoglycemic agent is selected from the group consisting of sulfonyl ureas, thiazolidine diones, alpha-glucosidase inhibitors, and insulin-releasing agents.

29. A method according to claim 20, wherein the mammal has non-insulin-dependent diabetes mellitus or insulin-dependent diabetes mellitus.

30. A method of treating a mammal having a diabetes condition, comprising:

administering a glycosylation-inhibiting agent to the mammal in an amount effective to inhibit hyperglycemia-associated pathological complications of the diabetes condition; and controlling moderately blood glucose concentrations in the mammal by administering a glucose-modulating agent to the mammal.

31. A method according to claim 30, wherein the glycosylation-inhibiting agent is a tetracycline compound.

32. A method according to claim 31, wherein the tetracycline compound is administered in an amount that has substantially no antimicrobial activity.

33. A method according to claim 31, wherein the tetracycline compound is:

4-de(dimethylamino)-tetracycline (CMT-1), 6-demethyl-6-deoxy-4-de(dimethylamino)-tetracycline (CMT-3), 4-de(dimethylamino)-12α-deoxytetracycline (CMT-7), or 6-deoxy-5α-hydroxy-4-de(dimethylamino)-tetracycline (CMT-8).

34. A method according to claim 30, wherein the glucose-modulating agent is insulin.

35. A method according to claim 34, wherein the method comprises administering insulin to the mammal in an amount or a frequency which is significantly lower than the amount or frequency normally required for mitigation of the hyperglycemia-associated pathological complications in the mammal.

36. A method according to claim 35, wherein the method comprises injecting insulin no more than an average of about twice daily.

37. A method according to claim 34, wherein the method further comprises administering an adjuvant hypoglycemic agent to the mammal.

38. A method according to claim 30, wherein the maintaining of the blood glucose concentration comprises administering a non-insulin hypoglycemic agent to the mammal.

39. A method according to claim 38, wherein the hypoglycemic agent is selected from the group consisting of sulfonyl ureas, thiazolidine diones, alpha-glucosidase inhibitors, and insulin-releasing agents.

* * * * *